United States Patent [19]

Schmidt et al.

[11] 4,134,978
[45] Jan. 16, 1979

[54] O-ALKYL-O-[8-CHLORO-QUINOXAL-2-YL]-THIONOALKANEPHOSPHONIC ACID ESTERS

[75] Inventors: Karl-Julius Schmidt; Hellmut Hoffmann, both of Wuppertal; Ingeborg Hammann, Cologne; Bernhard Homeyer, Leverkusen; Wilhelm Stendel, Wuppertal, all of Germany

[73] Assignee: Bayer Aktiengesellschaft, Leverkusen, Germany

[21] Appl. No.: 786,914

[22] Filed: Apr. 12, 1977

[30] Foreign Application Priority Data

Apr. 13, 1976 [DE] Fed. Rep. of Germany ....... 2616091

[51] Int. Cl.² .......................... C07D 9/65; A01N 9/36
[52] U.S. Cl. ..................... 424/200; 544/337
[58] Field of Search ............... 424/200; 260/250 QP; 544/337

[56] References Cited

U.S. PATENT DOCUMENTS 3,621,021  11/1971  Miller ............................ 260/250 QP
3,801,577   4/1974  Helfenberger ................ 260/250 QP
3,880,997   4/1975  Schmidt ........................ 260/250 QP
3,929,998  12/1975  Lovell ........................... 260/250 QP

FOREIGN PATENT DOCUMENTS 702672  8/1967  Belgium.

Primary Examiner—Nicholas S. Rizzo
Assistant Examiner—Mark L. Berch
Attorney, Agent, or Firm—Sprung, Felfe, Horn, Lynch & Kramer

[57] ABSTRACT

O-Alkyl-O-[8-chloro-quinoxal-2-yl]-thionoalkanephosphonic acid esters of the formula

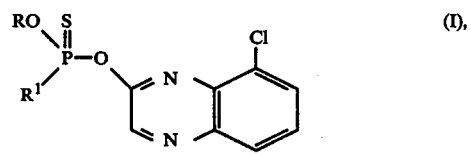

in which R and $R^1$ each independently is alkyl with 1 to 6 carbon atoms, which possess arthropodicidal, especially insecticidal and acaricidal, properties.

9 Claims, No Drawings

O-ALKYL-O-[8-CHLORO-QUINOXAL-2-YL]-THIONOALKANEPHOSPHONIC ACID ESTERS

The present invention relates to and has for its objects the provision of particular new O-alkyl-O-[8-chloro-quinoxal-2-yl]-thionoalkanephosphonic acid esters which possess arthropodicidal, especially insecticidal and acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from German Published Specification DOS 1,545,817 and Belgian Patent Specification 702,672 that certain O-quinoxalylthiono-phosphoric acid esters and phosphonic acid esters, for example O,O-diethyl-O-[quinoxal-2-yl]-thionophosphoric acid ester (Compound A) and O-ethyl-O-[6,8-dichloroquinoxal-2-yl]-thiono-methanephosphonic acid ester (Compound B), possess insecticidal and acaricidal properties.

The present invention now provides, as new compounds, the O-quinoxalylthionophosphonic acid esters of the general formula

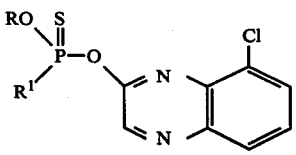

in which R and $R^1$ each independently is alkyl with 1 to 6 carbon atoms.

Preferably, R represents straight-chain or branched alkyl with 1 to 3 carbon atoms and $R^1$ represents methyl or ethyl.

Surprisingly, the O-quinoxalylthionophosphonic acid esters according to the invention possess a better insecticidal and acaricidal action than the compounds of analogous structure, and of the same type of action, previously known from the literature. The compounds according to the present invention thus represent a genuine enrichment of the art.

The present invention also provides a process for the preparation of an O-quinoxalylthionophosphonic acid ester of the formula (I) in which 8-chloro-2-hydroxyquinoxaline, of the formula

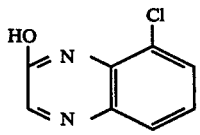

is reacted, either as such in the presence of an acid acceptor or in the form of an alkali metal salt, alkaline earth metal salt or ammonium salt thereof, with an O-alkylthionoalkanephosphonic acid ester halide of the general formula

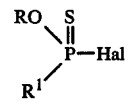

in which
R and $R^1$ have the abovementioned meanings and
Hal represents halogen, preferably chlorine, if appropriate in the presence of a solvent.

If, for example, O-iso-propylthionoethanephosphonic acid ester chloride and 8-chloro-2-hydroxyquinoxaline are used as starting materials, the course of the reaction can be represented by the following equation:

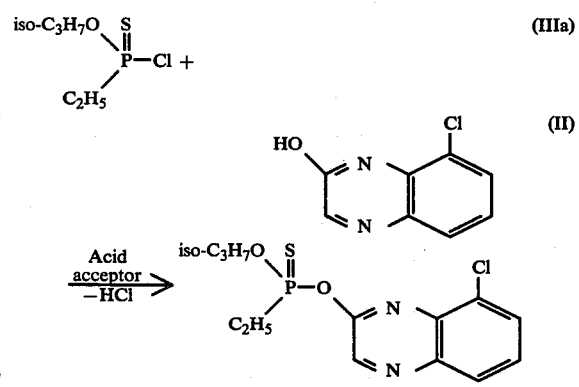

The O-alkylthionoalkanephosphonic acid ester halides (III) to be used as starting materials are known and can be prepared in accordance with customary processes.

The following may be mentioned as individual examples thereof: O-methyl-, O-ethyl-, O-n-propyl- and O-iso-propylmethane- and ethane-thionophosphonic acid ester halides, especially the chlorides.

8-Chloro-2-hydroxyquinoxaline (II) can be prepared in accordance with processes known from the literature, for example by starting from the known 6-chloro-2-nitro-aniline, reducing it and cyclizing the resulting diamide with glyoxylic acid semiacetal alkyl ester to give 8-chloro-2-hydroxyquinoxaline.

The process for the preparation of the compounds according to the invention is preferably carried out in the presence of a suitable solvent or diluent. Virtually all inert organic solvents can be used for this purpose, especially aliphatic and aromatic, optionally chlorinated, hydrocarbons such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is generally carried out at between 0° and 120° C., preferably at 15° to 60° C.

In general, the reaction is allowed to take place under normal pressure.

To carry out the process, the starting components are preferably employed in equimolar amounts. An excess of one or other component produces no significant advantages. The reactants are in general brought together in one of the stated solvents and in most cases stirred at an elevated temperature for one or more hours to complete the reaction. An organic solvent, for example toluene, is then added and the organic phase is worked up in the usual manner by washing, drying and distilling off the solvent. The compounds are obtained in a crystalline form and are characterized by their melting point.

As already mentioned, the O-quinoxalylthionophosphonic acid esters according to the invention are distinguished by an excellent insecticidal and acaricidal activity. They are not only active against plant pests, pests harmful to health and pests of stored products but also, in the veterinary medicine field, against animal parasites (ectoparasites), such as ticks and parasitic fly larvae. They combine a low phytotoxicity with a good action against both sucking and biting insects and mites.

For this reason, the compounds according to the invention can be employed successfully as pesticides in plant protection as well as in the hygiene field, the field of protection of stored products and the veterinary field.

The active compounds are well tolerated by plants, have a favorable level of toxicity to warm-blooded animals, and can be used for combating arthropod pests, especially insects and arachnids, which are encountered in agriculture, in forestry, in the protection of stored products and of materials, and in the hygiene field. They are active against normally sensitive and resistant species and against all or some stages of development. The abovementioned pests include:

from the class of the *Isopoda*, for example *Oniscus asellus, Armadillidium vulgare* and *Porcellio scaber;* from the class of the *Diplopoda*, for example *Blaniulus guttulatus;* from the class of the *Chilopoda*, for example *Geophilus carpophagus* and *Scutigera* spec.; from the class of the *Symphyla*, for example *Scutigerella immaculata;* from the order of the *Thysanura*, for example *Lepisma saccharina;* from the order of the *Collembola*, for example *Onychiurus armatus;* from the order of the *Orthoptera*, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the *Dermaptera*, for example *Forficula auricularia;* from the order of the *Isoptera*, for example *Reticulitermes* spp.; from the order of the *Anoplura*, for example *Phylloxera vastatrix, Pemphigus* spp., *Pediculus humanus corporis, Haematopinus* spp. and *Linognathus* spp.; from the order of the *Mallophaga*, for example *Trichodectes* spp. and *Damalinea* spp.; from the order of the *Thysanoptera*, for example *Hercinothrips femoralis* and *Thrips tabaci;* from the order of the *Heteroptera*, for example *Eurygaster* spp. *Dysdercus intermedius, Piesma quadrata, Cimex lectularius, Rhodnius prolixus* and *Triatoma* spp.; from the order of the *Homoptera*, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.; from the order of the *Lepidoptera*, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., Pyrausta nubilalis, Ephestia kuehniella, Galleria mellonella, Cacoecia podana, Capua reticulana, Choristoneura fumiferana, Clysia ambiguella, Homona magnanima and *Tortrix viridana;* from the order of the *Coleoptera*, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., Otiorrhynchus sulcatus, Cosmopolites sordidus, Ceuthorrhynchus assimilis, Hypera postica, Dermestes spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica;* from the order of the *Hymenoptera*, for example *Diprion* spp., *Hoplocampa* spp., *Lasius* spp., *Monomorium pharaonis* and *Vespa* spp.; from the order of the *Diptera*, for example *Aedes* spp., *Anopheles* spp., *Culex* spp., *Drosophila melanogaster, Musca* spp., Fannia spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa;* from the order of the *Siphonaptera*, for example *Xenopsylla cheopis*, and *Ceratophyllus* spp.; from the class of the *Arachnida*, for example *Scorpio maurus* and *Latrodectus mactans;* from the order of the *Acarina*, for example *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp.

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, dichlorodifluoromethane or trichlorofluoromethane, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides, or nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling arthropods, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal to be freed of ectoparasites, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

*Laphygma* test
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cotton leaves (*Gossypium hirsutum*) were sprayed with the preparation of the active compound until dew-moist and were then infested with caterpillars of the owlet moth (*Laphygma exigua*).

After the specified periods of time, the destruction in % was determined. 100% meant that all the caterpillars had been killed, whereas 0% meant that no caterpillars had been killed.

The active compounds, the concentrations of the active compound, the evaluation times and the results can be seen from the following table:

Table 1
(Laphygma Test)

| Active compound | Active compound concentration in % | Degree of destruction in % after 3 days |
|---|---|---|
| (known) (B) [CH$_3$, C$_2$H$_5$O, P(=S)–O–pyrimidine–2,4-dichlorophenyl] | 0.1<br>0.02 | 100<br>0 |
| (3) [CH$_3$, C$_2$H$_5$O, P(=S)–O–pyrimidine–2-chlorophenyl] | 0.1<br>0.02 | 100<br>100 |
| (2) [CH$_3$, iso-C$_3$H$_7$O, P(=S)–O–pyrimidine–2-chlorophenyl] | 0.1<br>0.02 | 100<br>100 |
| (1) [C$_2$H$_5$, C$_2$H$_5$O, P(=S)–O–pyrimidine–2-chlorophenyl] | 0.1<br>0.02 | 100<br>100 |

EXAMPLE 2

*Myzus* test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% meant that all the aphids were killed, whereas 0% meant that none of the aphids were killed.

The active compounds, the concentrations of the active compounds, the evaluation times and the results can be seen from the following table:

Table 2
(Myzus test)

| Active compound | Active compound concentration in % | Degree of destruction in % after 1 day |
|---|---|---|
| 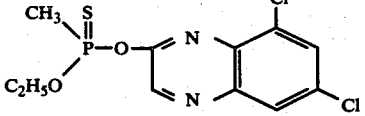 (known) (B) | 0.02<br>0.004<br>0.0008 | 100<br>60<br>0 |
| 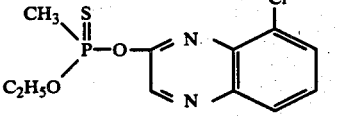 (3) | 0.02<br>0.004<br>0.0008 | 100<br>100<br>95 |
| 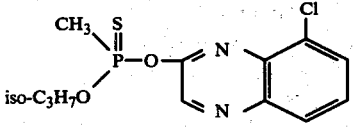 (2) | 0.02<br>0.004<br>0.0008 | 100<br>100<br>90 |
| 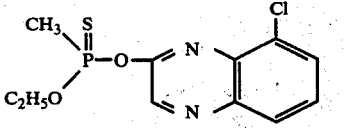 (1) | 0.02<br>0.004<br>0.0008 | 100<br>100<br>99 |

EXAMPLE 3

*Tetranychus* test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all the spider mites were killed, whereas 0% meant that none of the spider mites were killed.

The active compounds, the concentrations of the active compounds, the evaluation times and the results can be seen from the following table:

Table 3
(Tetranychus Test)

| Active compound | Active compound concentration in % | Degree of destruction in % after 2 days |
|---|---|---|
| 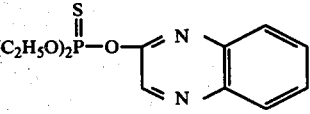 (known) (A) | 0.02<br>0.004<br>0.0008 | 98<br>55<br>0 |
| 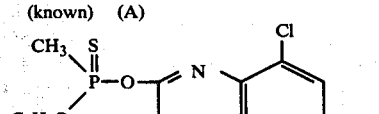 (known) (B) | 0.02<br>0.004<br>0.0008 | 100<br>40<br>0 |
| 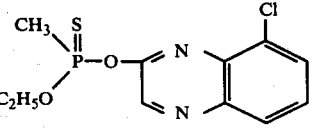 (3) | 0.02<br>0.004<br>0.0008 | 100<br>100<br>60 |

Table 3-continued
(Tetranychus Test)

| Active compound | Active compound concentration in % | Degree of destruction in % after 2 days |
|---|---|---|
| CH$_3$(S)(iso-C$_3$H$_7$O)P—O—[pyrazinyl-Cl] (2) | 0.02<br>0.004<br>0.0008 | 100<br>100<br>98 |

EXAMPLE 4

Critical concentration test/soil insects
Test insects: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (=mg/l). The soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all the test insects had been killed and was 0% if exactly as many test insects were still alive as in the case of the untreated control.

The active compounds, amounts used and results can be seen from the table which follows:

(Critical concentration test/soil insects)
*Phorbia antiqua* grubs in the soil

| Active compound | Degree of destruction in % at an active compound concentration of 20 ppm |
|---|---|
| CH$_3$(S)(C$_2$H$_5$O)P—O—[pyrazinyl-Cl,Cl] (known) (B) | 0 |
| C$_2$H$_5$(S)(C$_2$H$_5$O)P—O—[pyrazinyl-Cl] (1) | 100 |
| CH$_3$(S)(C$_2$H$_5$O)P—O—[pyrazinyl-Cl] (3) | 100 |
| CH$_3$(S)(iso-C$_3$H$_7$O)P—O—[pyrazinyl-Cl] (2) | 100 |

EXAMPLE 5

Test on symbovine flies
Test on adult *Musca autumnalis*/dish test in vitro
Test insect: Unfed 1-day-old flies (*Musca autumnalis*)

Test procedure: 10 flies (stunned with CO$_2$) per concentration were transferred onto filter paper discs (diameter 7.5 cm), impregnated with active compound, and located in Petri dishes (polystyrene). The treated discs were prepared by pipetting 1 ml of active compound formulation at the concentration to be tested (100, 30, 10 or 3 ppm) onto the discs. The dishes were then transferred to, and stored in, a climatically controlled test room (27° C. ± 1° C., 70% relative humidity ± 5%). The action was checked after ½, 1, 2, 4, 8 and 24 hours.

Test criterion: The test criterion was the occurrence of death of the treated flies (sign of death = absence of voluntary movements of the limbs after stimulation with a dissecting needle).

Rating
3 = 100% action = all the flies were dead
2 = >50% action = >50% of the flies were dead
1 = <50% action = <50% of the flies were dead
0 = no action = all the flies were alive.

The active compounds examined, the active compound concentrations tested and the results obtained can be seen from the following table:

Table 5

Test on symbovine flies
(*Musca autumnalis*)

| Active compound | Active compound concentration in ppm | Rating |
|---|---|---|
| $C_2H_5$–$\overset{S}{\underset{\|}{P}}$(–$OC_2H_5$)–O–[pyrimidine-Cl-phenyl] (1) | 1,000 | 3 |
| | 300 | 3 |
| | 100 | 3 |
| | 30 | 2 |

EXAMPLE 6

Gadfly test

Test on adult *Stomoxys calcitrans*/dish test in vitro

Test insect: Unfed 1-day-old flies (*Stomoxys calcitrans*)

Test procedure: 10 flies (stunned with $CO_2$) per concentration were transferred onto filter paper discs (diameter 7.5 cm), impregnated with active compound, and located in Petri dishes (polystyrene). The treated discs were prepared by pipetting 1 ml of active compound formulation at the concentration to be tested (100, 30, 10 or 3 ppm) onto the discs. The dishes were then transferred to, and stored in, a climatically controlled test room (27° C. ± 1° C., 70% relative humidity ± 5%). The action was checked after ½, 1, 2, 4, 8 and 24 hours.

Test criterion: The test criterion was the occurrence of death of the treated flies (sign of death = absence of voluntary movements of the limbs after stimulation with a dissecting needle).

Rating

3 = 100% action = all the flies were dead
2 = >50% action = >50% of the flies were dead
1 = <50% action = <50% of the flies were dead
0 = no action = all the flies were alive.

The active compounds examined, the active compound concentrations tested and the results obtained can be seen from the following table:

Table 6

Gadfly Test
(*Stomoxys calcitrans*)

| Active compound | Active compound concentration in ppm | Rating |
|---|---|---|
| $C_2H_5$–$\overset{S}{\underset{\|}{P}}$(–$OC_2H_5$)–O–[pyrimidine-Cl-phenyl] (1) | 1,000 | 3 |
| | 300 | 3 |
| | 100 | 2 |
| | 30 | 2 |

EXAMPLE 7

Tick test

Screening test on *Boophilus microplus*/immersion test in vitro

Test acarid: Fully bloated, female, adult cattle ticks (*Boophilus microplus*), which were collected shortly before they would have become detached from the host animal.

Test Procedure: 10 ticks were immersed for each concentration in a concentration series (10,000, 3,000, 1,000, 300, 100 and 30 ppm). The immersion time was 1 minute, with continuous shaking in a shaking apparatus (96 revolutions per minute). The acarids were then transferred into beakers and kept in a climatically controlled room (28° C. ± 1° C., 80% relative humidity ± 10%). Both the immediate action, after 24 hours, and the long-term action, after 7 days, were checked.

Test criteria: the criteria of the activity were the occurrence of voluntary movements of the body and limbs (as far as immediate action was concerned) and the inhibition of laying of fertile eggs (as far as the long-term action was concerned).

Rating

3 = 100% action = no voluntary movement detectable, and complete inhibition of laying of eggs.
2 = >50% action = no locomotion detectable and/or more than 50% inhibition of the laying of eggs.
1 = <50% action = no coordinated locomotion detectable and/or less than 50% inhibition of the layer of eggs.
0 = no action = normal sequence of movements detectable and normal amounts of eggs laid.

The active compounds investigated, the concentrations tested and the results obtained can be seen from the following table:

Table 7

(Tick test - *Boophilus microplus*, (resistant))

| Active compound | Active compound concentration in ppm | Rating |
|---|---|---|
| $C_2H_5$–$\overset{S}{\underset{\|}{P}}$(–$OC_2H_5$)–O–[pyrimidine-Cl-phenyl] (1) | 10,000 | 3 |
| | 1,000 | 2 |
| | 300 | 2 |
| | 100 | 2 |

EXAMPLE 8

Blowfly larvae test

Screening test on *Lucilia cuprina*/tube test in vitro

Test insect: Freshly hatched, about 12-24-hours-old sensitive blowfly larvae (*Lucilia cuprina*).

Test Procedure: About 20 to 30 larvae were employed per concentration in concentration series (100, 10 or 1 ppm). For this purpose, larvae were placed on cottonwool plugs (diameter 1.7 cm, height 1 cm) contained in glass tubes (white diffusing glasses, 43/44 × 23/24 mm, made from Bunder glass), the plugs having been moistened beforehand with 2.5 ml of a 25% strength slurry of bonemeal in water. 0.5 ml of the concentration to be tested was then pipetted onto these moistened cottonwood plugs. The samples were then transferred to, and kept in, a climatically controlled room (27° C. ± 1° C., 70% relative humidity ± 5%). The action was checked after 24 hours.

Test criterion: The criterion of the activity was the occurrence of death of the treated larvae.

Rating

3 = 100% action = all the larvae were dead
2 = >50% action = >50% of the larvae were dead
1 = <50% action = <50% of the larvae were dead
0 = no action = all the larvae were alive.

The active compounds examined, the concentrations tested and the test results obtained can be seen from the following table:

Table 8

Blowfly larvae test
*(Lucilia cuprina,* resistance)

| Active compound | Active compound concentration in ppm | Rating |
|---|---|---|
| (1) structure with C₂H₅, C₂H₅O, P=S, O, Cl-quinoxaline | 100<br>30<br>10<br>3<br>1 | 3<br>3<br>3<br>3<br>3 |
| (3) structure with CH₃, C₂H₅O, P=S, O, Cl-quinoxaline | 100<br>10<br>1 | 3<br>3<br>3 |
| (2) structure with CH₃, iso-C₃H₇O, P=S, O, Cl-quinoxaline | 100<br>10 | 3<br>3 |

The process of this invention is illustrated by the following preparative examples:

EXAMPLE 9

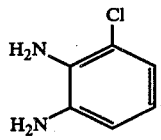
(a)

1,360 g (8 mol) of 6-chloro-2-nitroaniline were dissolved in 7 l of methanol and reduced in the usual manner, using Raney nickel as the catalyst. The solution was separated from the Raney nickel by filtration and the resulting diaminochlorobenzene was directly processed further.

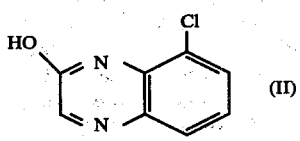
(II)
(b)

100 ml of triethylamine were added to the reduction product of 6-chloro-2-nitroaniline in methanol (assumed to be 8 mol), obtained as described under (a). The mixture was then heated to 50° C. 1,168 g (8 mol) of glyoxylic acid semiacetal ester were then added dropwise, over the course of 2 hours, to the mixture, thereby causing a slight exothermic reaction. The mixture was boiled for 2 hours under reflux, whereupon a solid product separated out. After 2 hours, the mixture was cooled to 0° C. and the precipitate was filtered off. 110 g (7.6% of theory) of 8-chloro-2-hydroxy-quinoxaline were obtained in the form of a light gray powder of melting point above 250° C. The mother liquor was concentrated, ether was added and the residue was filtered off. A further 583 g (40.6% of theory) were thus obtained.

Accordingly, the total yield was 693 g (48% of theory).

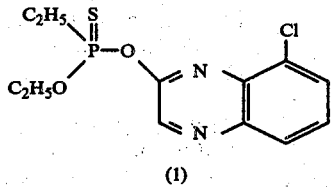
(1)
c)

36 g (0.2 mol) of 8-chloro-2-hydroxy-quinoxaline together with the equimolar amount of dry potassium carbonate, in 250 ml of acetonitrile, were heated for 30 minutes under reflux, while stirring, and 34 g (0.2 mol) of O-ethylthionoethanephosphonic acid ester chloride were then added dropwise to the reaction mixture at 40° C. The latter was stirred for a further 3 to 4 hours at room temperature. 500 ml of toluene were then added to the mixture and the toluene solution was washed with water and then with about 5% strength sodium hydroxide solution in order to remove any quinoxaline which may have been present. After the toluene solution had been washed until neutral, it was dried, the solvent was evaporated off and the residue thus obtained was recrystallized from ethanol. 51 g (80.5% of theory) of O-ethyl-O-[8-chloroquinoxal-2-yl]-thionoethanephosphonic acid ester were thus obtained as white crystals of melting point 57° C.

The following compounds could be prepared analogously:

| Compound No. | Formula | Melting point (° C) | Yield (% of theory) |
|---|---|---|---|
| 2 | CH₃, iso-C₃H₇O, P=S, O-quinoxaline-Cl | 60 | 73 |

| Compound No. | Formula | Melting point (°C) | Yield (% of theory) |
|---|---|---|---|
| 3 | 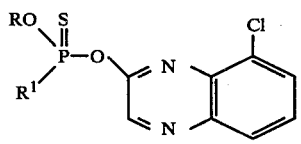 | 67 | 62 |

It will be appreciated that the instant specification and examples are set forth by way of illustration and not limitation, and that various modifications and changes may be made without departing from the spirit and scope of the present invention.

What is claimed is:

1. An O-alkyl-O-[8-chloro-quinoxal-2-yl]-thionoalkanephosphonic acid ester of the formula

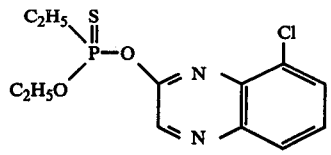

in which

R and R¹ each independently is alkyl with 1 to 6 carbom atoms.

2. An ester according to claim 1, in which R is straightchain or branched alkyl with 1 to 3 carbon atoms and R¹ is methyl or ethyl.

3. An ester according to claim 1, wherein such ester is O-ethyl-O-[8-chloroquinoxal-2-yl]-thionoethanephosphonic acid ester of the formula 4. An ester according to claim 1, wherein such ester is O-isopropyl-O-[8-chloroquinoxal-2-yl]-thionomethanephosphonic acid ester of the formula

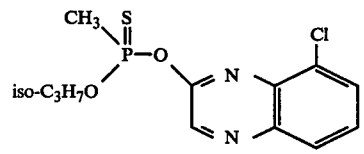

5. An ester according to claim 1, wherein such ester is O-ethyl-O-[8-chloroquinoxyal-2-yl]-thionomethanephosphonic acid ester of the formula

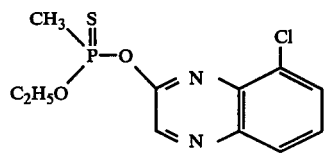

6. An insecticidal or acaricidal composition containing as active ingredient an insecticidally or acaricidally effective amount of an ester according to claim 1 in admixture with a diluent.

7. A method of combating insects or acarids which comprises applying to the insects or acarids or to a habitat thereof, an insecticidally or acaricidally effective amount of an ester according to claim 1.

8. The method according to claim 7, wherein the ester is applied to a domesticated animal.

9. The method according to claim 7, wherein such compound is
O-ethyl-O-[8-chloroquinoxal-2-yl]-thionoethanephosphonic acid ester,
O-isopropyl-O-[8-chloroquinoxal-2-yl]-thionomethanephosphonic acid ester, or
O-ethyl-O-[8-chloroquinoxal-2-tl]-thionomethanephosphonic acid ester.

* * * * *

UNITED STATES PATENT AND TRADEMARK OFFICE
CERTIFICATE OF CORRECTION

PATENT NO. : 4,134,978
DATED : January 16, 1979
INVENTOR(S) : Karl-Julius Schmidt et al It is certified that error appears in the above-identified patent and that said Letters Patent are hereby corrected as shown below:

| | |
|---|---|
| Col. 4, line 38 | Delete "Aedes", substitute --Aëdes--. |
| Col. 9, Table 2, compound 1 | Delete "$CH_3$", substitute --$C_2H_5$--. |
| Col. 14, line 51 | Delete "Bunder", substiute --Bünder--. |
| Col. 15, line 2 | Delete "resistance", substitute --resistant--. |

Signed and Sealed this

Seventeenth Day of July 1979

[SEAL]

Attest:

LUTRELLE F. PARKER
Attesting Officer   Acting Commissioner of Patents and Trademarks